United States Patent [19]
Reid

[11] Patent Number: 4,632,134
[45] Date of Patent: Dec. 30, 1986

[54] ARTIFICIAL FINGERNAIL CONSTRUCTION

[75] Inventor: Georgianna Reid, Prairie Village, Kans.

[73] Assignee: LaCuticle, Inc., Kansas City, Mo.

[21] Appl. No.: 846,830

[22] Filed: Apr. 1, 1986

Related U.S. Application Data

[63] Continuation of Ser. No. 679,483, Dec. 7, 1984, abandoned.

[51] Int. Cl.$^4$ .............................................. A45D 29/00
[52] U.S. Cl. ...................................................... 132/73
[58] Field of Search ........................ 132/73, 88.5, 88.7

[56] References Cited

U.S. PATENT DOCUMENTS

| | | | |
|---|---|---|---|
| 3,502,088 | 3/1970 | Jarby | 132/73 |
| 4,007,748 | 2/1977 | Matranga et al. | 132/73 |
| 4,157,095 | 6/1979 | Sweet | 132/73 |
| 4,222,399 | 9/1980 | Ionescu | 132/73 |
| 4,299,243 | 11/1981 | Umstattd | 132/73 |
| 4,407,310 | 10/1983 | Jadow | 132/73 |

Primary Examiner—Robert Peshock
Attorney, Agent, or Firm—Schmidt, Johnson, Hovey & Williams

[57] ABSTRACT

An improved method of applying an artificial fingernail to a natural fingernail is provided which results in a strong, durable artificial fingernail having a natural appearance. The method preferably includes the steps of securing an artificial fingernail extension to a natural fingernail and then adhering a strengthening layer of linen over the entire upper fingernail surface. An adhesive coating is applied over the linen layer and is buffed to present a smooth, thin, finished fingernail surface.

6 Claims, 6 Drawing Figures

ARTIFICIAL FINGERNAIL CONSTRUCTION

This application is a continuation of application Ser. No. 06/679,483, filed 12/07/84 now abandoned.

BACKGROUND OF THE INVENTION

1. Field of the Invention

This invention relates to a method of applying an artificial fingernail to a natural fingernail. More particularly, it is concerned with an improved method of securing an extension, in the form of an artificial fingernail, to a natural fingernail, which includes the step of adhesively adhering a layer of linen over the upper surface of the artificial fingernail after it has been initially secured in place over the natural fingernail. The linen and adhesive lamination is subsequently smoothed to present a finished fingernail surface.

2. Description of the Prior Art

The method of applying artificial fingernails to natural fingernails is a conventional practice that provides a longer, more attractive fingernail for those who cannot grow their own nails.

One present method of applying artificial fingernails includes the step of only adhering an artificial fingernail over essentially the entire natural fingernail surface and extending a length therefrom. As can be appreciated, the artificial nail be be strong enough to endure daily wear and of sufficient thickness to prevent breakage. This results in the artificial fingernail appearing thicker and less natural than a relatively thin, normal or natural fingernail. Another difficulty with this method is that the artificial fingernail does not remain effectively secured to a natural fingernail and tends to snap off. An additional problem related to this type of plastic artificial fingernail is that it results in damage to the natural fingernail due to a fungus growth between the artificial and natural fingernails.

U.S. Pat. No. 4,135,526 issued Jan. 23, 1979, illustrates an artificial fingernail extension which includes a nail-engaging recess in the artificial fingernail that conforms to the shape of the forward edge of the natural fingernail. The recess facilitates the application of the fingernail extension to a natural fingernail. The reduced covering area of this fingernail extension prevents fungus growth damage to the natural fingernail. However, a problem arises with this type of fingernail extension in that, to present a finished, level fingernail surface, layers of adhesive are gradually built up on the upper fingernail surface to disguise the joint between the artificial and natural fingernails and provide a stronger artificial fingernail. As pointed out above, this type of artificial fingernail appears unnatural due to its necessary thickness and bulk.

SUMMARY OF THE INVENTION

The problems outlined above are solved by the present method of applying an artificial fingernail extension which is easily and quickly completed to present a finished, naturally appearing, strong, but yet thin, artificial fingernail.

The method, as practiced, broadly includes the process of securing an artificial fingernail extension in overlying relationship to a natural fingernail and then adhering a layer of linen over essentially the entire upper surface of the artificial and natural fingernails to provide a thin, strong artificial fingernail surface. The linen is coated with an adhesive and both the adhesive and linen layers, as a lamination, are smoothed to present a finished surface.

The problems associated with prior artificial fingernail attachment methods are overcome by the present method of applying a thin, flexible, porous layer of linen over an artificial fingernail extension.

DESCRIPTION OF THE PREFERRED EMBODIMENT

Figure 1:
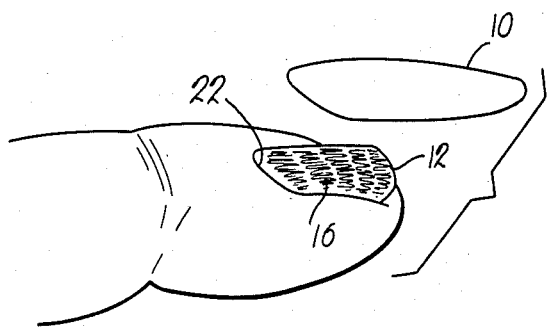
FIG. 1 is a perspective, exploded view illustrating the application of an artificial fingernail extension to a natural fingernail.
Figure 2:
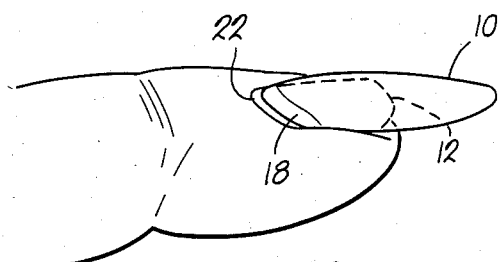
FIG. 2 is a perspective view of the artificial fingernail extension secured to a natural fingernail and illustrating the beveled joint between the artificial and natural fingernails.
Figure 3:
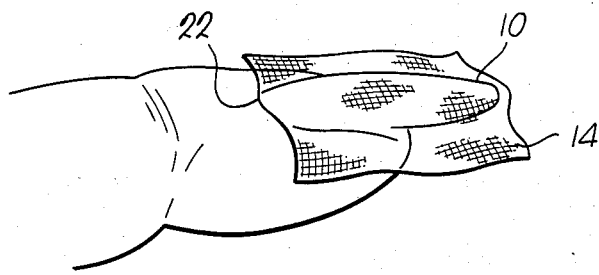
FIG. 3 is a perspective view illustrating a layer of linen placed over essentially the entire upper surface of the artificial and natural fingernails.

Referring now to the drawing, a method of applying an artificial fingernail extension 10 to a natural fingernail 12 in accordance with the invention broadly includes the steps of: (a) applying an artificial fingernail extension 10 in substantially covering relationship to a natural fingernail 12; (b) securing a layer of linen 14 over essentially the entire artificial and natural fingernails 10, 12; (c) coating the linen 14 with an adhesive sealant 24; and (d) smoothing the coated linen 14 to present a finished surface.

In more detail, as shown in FIG. 1, the method of applying an artificial fingernail extesnion 10 to a natural fingernail 12 preferably begins with the step of cleaning the natural fingernail with an acetone solution (not shown) and roughing the natural fingernail with an emery board or the like.

To attach the artificial fingernail extension 10 to the natural fingernail 12, a quick-drying liquid adhesive 16 such as an ethyl alpha cyanoacrylate adhesive is applied to the underside of the artificial fingernail extension 10 and to the upper surface of the natural fingernail 12. The artificial fingernail 10 is placed over the natural fingernail 12.

Upon quick drying of the adhesive 16 (approximately five seconds) the artificial fingernail extension 10 is firmly bonded to the natural fingernail 12. The joint 18 formed between the inner edge of the artificial fingernail extension 10 and the natural fingernail 12 is beveled to present a smoothly contoured surface which blends the natural and artificial nails together.

Additional adhesive 20 is applied over the entire upper surface of the artificial and natural fingernails 10, 12, but not over the sensitive surface of the fingernail 12 directly adjacent the cuticle 22.

A layer of linen 14 is applied over the entire nail surface and secured thereto with adhesive 20. The linen is preferably a fine, soft, sheer open-weave type of material, such as Batiste.

It is also desirable that the linen be previously treated to remove the flax which is normally found therein. This may be accomplished by soaking the linen in a product such as Woolite for three or four days and then running it through a washing machine, drying it and then cutting it into strips before application.

After application, the linen 14 may then be trimmed, as by scissors, to conform to the shape of the artificial and natural fingernails 10, 12.

Additional adhesive 24 is then applied over the linen surface 14 to strengthen the bonded attachment. The adhesive 24 should dry for approximately 30 seconds to insure that it is properly cured.

Figure 4:
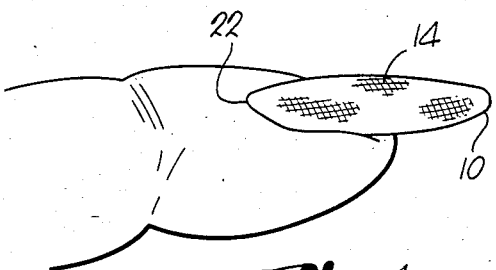
FIG. 4 is a view similar to FIG. 3 in which the linen has been trimmed to conform to the shape of the fingernail.
Figure 5:
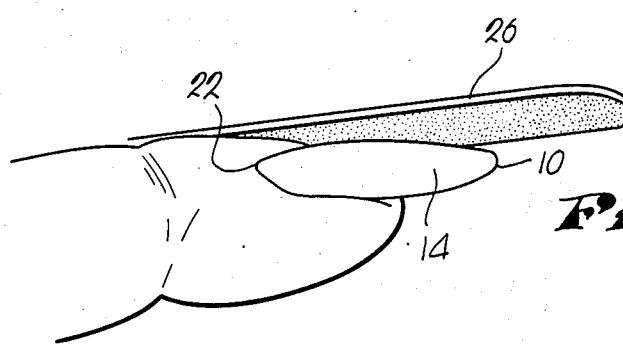
FIG. 5 is a perspective view illustrating the step of smoothing the linen layer.
Figure 6:
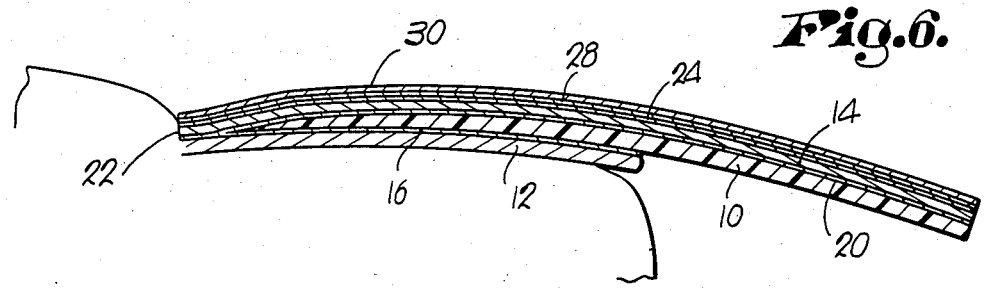
FIG. 6 is an enlarged vertical central cross-sectional view of the finished fingernail illustrating the layers applied to the natural fingernail.

As shown in FIG. 4, the resulting textured linen-adhesive surface is ready for the final finishing process. The upper surface of the coated linen 14 is then smoothed with an emery board 26 as shown in FIG. 5. A final layer of quick-drying adhesive 28 is applied over the entire surface of the nail and is dried for approximately five seconds. The nail surface is again smoothed with a finer emery board until the surface is sufficiently smooth and polished. A final coating of fingernail polish 30 may be applied to the fingernail.

It will be appreciated that the method as outlined above can also be used to strengthen a natural fingernail. In this case, the linen is applied directly to the natural fingernail surface without the need of an artificial fingernail extension and the process is completed as set out above.

I claim:

1. An artificial fingernail construction for attachment to a natural fingernail and comprising:
   an artifical fingernail extension of size and shape to substantially cover said natural fingernail and extend outwardly therefrom;
   an adhesive for securing said extension to said natural fingernail in said substantially covering relationship;
   a layer of linen conformably covering essentially the entire, normally uppermost, exposed surface of the extension and natural fingernail; and
   an adhesive sealant coating said linen layer for bonding the linen layer to said extension and sealing the normally upper surface of the linen layer.

2. The construction of claim 1, said extension being beveled at the joint formed between the inner edge of said extension and said natural fingernail, to present a smoothly contoured surface which blends the natural nail and extension together.

3. The construction of claim 1, said adhesive comprising a cyanoacrylate adhesive material.

4. The construction of claim 1, said adhesive sealant comprising a cyanoacrylate adhesive material.

5. The construction of claim 1, said linen layer being substantially free of flax.

6. The construction of claim 1, there being multiple layers of said adhesive sealant applied over said linen layer.

* * * * *